(12) United States Patent
Gottesman et al.

(10) Patent No.: US 8,438,039 B2
(45) Date of Patent: May 7, 2013

(54) USER CUSTOMIZABLE WORKFLOW PREFERENCES FOR REMOTE PATIENT MANAGEMENT

(75) Inventors: Janell M. Gottesman, St. Louis Park, MN (US); James E. Willenbring, St. Paul, MN (US); David J. Scheffler, Lino Lakes, MN (US); John P. VanDanacker, Greenfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 1956 days.

(21) Appl. No.: 11/115,626

(22) Filed: Apr. 27, 2005

(65) Prior Publication Data

US 2006/0247709 A1 Nov. 2, 2006

(51) Int. Cl.
*G06Q 10/00* (2012.01)

(52) U.S. Cl.
USPC .................................. 705/2; 705/3

(58) Field of Classification Search ........... 705/2
See application file for complete search history.

(56) References Cited

U.S. PATENT DOCUMENTS

| | | | |
|---|---|---|---|
| 5,312,453 A | 5/1994 | Shelton et al. | 607/19 |
| 5,438,408 A | 8/1995 | Weichert et al. | 356/336 |
| 5,545,186 A | 8/1996 | Olson et al. | 607/14 |
| 5,752,976 A | 5/1998 | Duffin et al. | 607/32 |
| 5,987,352 A | 11/1999 | Klein et al. | 600/509 |
| 6,169,925 B1 | 1/2001 | Villaseca et al. | 607/60 |
| 6,240,317 B1 | 5/2001 | Villaseca et al. | 607/60 |
| 6,249,703 B1 | 6/2001 | Stanton et al. | 607/30 |
| 6,250,309 B1 | 6/2001 | Krichen et al. | 128/899 |
| 6,418,346 B1 * | 7/2002 | Nelson et al. | 607/59 |
| 6,442,433 B1 * | 8/2002 | Linberg | 607/60 |
| 6,471,645 B1 | 10/2002 | Warkentin et al. | 600/300 |
| 6,480,745 B2 | 11/2002 | Nelson et al. | 607/60 |
| 6,482,154 B1 | 11/2002 | Haubrich et al. | 600/300 |
| 6,561,975 B1 | 5/2003 | Pool et al. | 600/300 |
| 6,564,104 B2 | 5/2003 | Nelson et al. | 607/60 |
| 6,574,511 B2 | 6/2003 | Lee | 607/60 |
| 6,599,250 B2 | 7/2003 | Webb et al. | 600/483 |
| 6,647,299 B2 | 11/2003 | Bourget | 607/60 |
| 7,324,949 B2 * | 1/2008 | Bristol | 705/3 |
| 2003/0149598 A1 | 8/2003 | Santoso et al. | 705/2 |
| 2004/0122701 A1 | 6/2004 | Dahlin et al. | 705/2 |
| 2004/0127958 A1 | 7/2004 | Mazar et al. | |
| 2005/0060186 A1 * | 3/2005 | Blowers et al. | 705/2 |
| 2005/0222631 A1 * | 10/2005 | Dalal et al. | 607/27 |
| 2006/0020491 A1 * | 1/2006 | Mongeon et al. | 705/2 |

FOREIGN PATENT DOCUMENTS

EP 1310272 5/2003

* cited by examiner

*Primary Examiner* — Hiep V Nguyen
(74) *Attorney, Agent, or Firm* — Michael C. Soldner

(57) ABSTRACT

A remote patient management system and method are provided including customizable workflow preferences. The method includes storing a user-programmed or "best practices" set of workflow operations, receiving a remote medical device data transmission, selecting a workflow preference in response to information contained in or relating to the data transmission, and performing remote patient management operations according to the selected workflow preference.

24 Claims, 8 Drawing Sheets

USER CUSTOMIZABLE WORKFLOW PREFERENCES FOR REMOTE PATIENT MANAGEMENT

FIELD OF THE INVENTION

The present invention relates generally to remote patient management systems and in particular to a remote patient management system that provides user-customizable workflow for controlling patient management operations performed by the system.

BACKGROUND OF THE INVENTION

Implantable medical devices (IMDs) such as cardiac pacemakers, cardioverters and defibrillators (ICDs), hemodynamic monitors, and drug delivery devices, are being offered with increasing capacity for storing physiological and device performance data. The use of home monitoring instrumentation and equipment, e.g., to measure weight, systemic blood pressure, symptoms, etc., is gaining popularity for managing patients with chronic illnesses. Physiological sensors for monitoring various patient conditions such as heart rhythm, blood pressure, respiration, patient activity level, heart wall motion, and blood chemistry may operate in conjunction with an IMD and home based instrumentation for acquiring continuous or periodic physiological data for processing and/or storage by the IMD or for clinical management. Such data may be used by the IMD in automated therapy delivery or by a clinician in diagnosing or monitoring a patient condition and in his or her therapy management.

Typically, a pacemaker or ICD patient is seen once every three to six months, as long as they are not experiencing adverse symptoms, in order to collect and review data stored by the device. In many cases, no clinical action is required. The development of remote patient monitoring systems that allow IMD data to be transferred from the patient's IMD to a home monitor and from the home monitor to a central database (or from the IMD directly to the central database) allows a clinician to reduce the required number of scheduled office visits when a patient is doing well and still maintain an up-to-date review of device performance and stored physiological data.

With the unprecedented amount of clinical data available from IMDs, and in-home external medical devices, a clinician has a mounting task in tracking and analyzing each patient's data in order to recognize events or conditions of clinical importance or concern. Remote monitoring of patients potentially enables a clinician to increase the number of patients he or she is treating by reducing the number of unnecessary office visits. However, having more patients monitored remotely increases the amount of data the clinician is responsible for tracking. Therefore, as remote patient monitoring systems become more widely used and the number of patient's having implantable or in-home external medical devices increases, the need arises for remote monitoring systems and data management methods that streamline patient management workload for the clinician while enabling the clinician to maintain thorough patient care.

BRIEF SUMMARY OF THE INVENTION

The present invention is directed toward a remote patient management system that provides customizable workflow settings for controlling patient management operations. Operations performed by a remote patient management system can include, but is not limited to, distribution of medical device transmissions, display of transmission data, data processing and analysis, scheduling tasks, communication tasks, and programming of the remote medical device. In accordance with the invention, the methods and prioritization of operations employed by the remote patient management system are customized by a user. In one embodiment, workflow is customized by a user according to personal preferences. In another embodiment, workflow is customized according to "best practices" settings stored in the patient management system according to typical recommended or frequently used workflow.

One aspect of the present invention is a remote patient management system including a remote medical device enabled for communication with a central programmer via a communication network. The networked central programmer includes a processor that operates in association with a central database used for storing patient data and for storing programs and parameters used by the processor for executing various patient management operations. The system includes a user interface, typically a graphical user interface, and associated code for allowing a user to enter or program customized remote patient management workflow settings stored in the central programmer database. The customized workflow is executed by the central programmer in response to receiving a medical device transmission.

Another aspect of the present invention is a method for remote patient management. The method includes programming user-customized workflow preferences in a central programmer database for use by a central programmer processor in controlling remote patient management operations. The method further includes receiving a remote medical device transmission by the central programmer and responding to the transmission by selecting a customized workflow based on information contained in or relating to the transmission. The method further includes executing remote patient management operations according to the customized workflow.

Another aspect of the present invention is a set of instructions stored in a computer-readable medium which when implemented by a remote patient management system cause the system to execute a set of remote patient management operations according to previously programmed user-customized workflow preferences. The system executes the set of remote patient management operations in response to receiving a remote medical device transmission by a central programmer and selects the set of remote patient management operations based on the information contained in or relating to the remote medical device transmission.

DETAILED DESCRIPTION OF THE INVENTION

Figure 1:
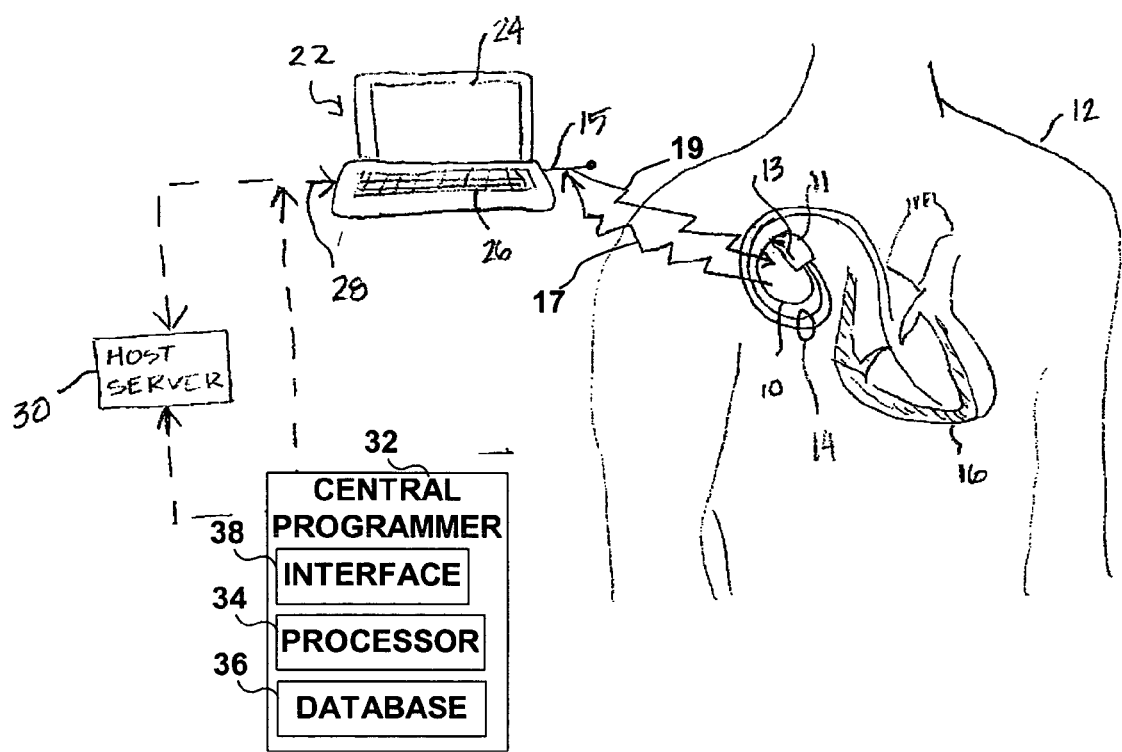
FIG. 1 is a schematic diagram of a remote patient management system.

FIG. 1 is a schematic diagram of a remote patient management system. The system includes a central programmer 32 enabled to receive data transmissions from multiple remote medical devices for enabling remote patient management of a population of patients. For example, central programmer 32 may be enabled to receive data transmission from an implantable medical device (IMD) 10 and/or an external medical device (EMD) 22. EMD 22 can be embodied as a remote home monitor or programmer used for communicating with IMD 10 and transferring IMD data to central programmer 32.

IMD 10 is shown implanted in the body of a patient 12. The present invention may be implemented for use with a variety of programmable IMDs, including cardiac stimulation devices, cardiac or other physiological monitoring devices, neuromuscular stimulators, implantable drug pumps, or the like. For the sake of illustration, IMD 10 is shown here as a cardiac stimulation device coupled to a set of leads 14 used for positioning electrodes and optionally other physiological sensors in operative relation to the patient's heart 16. Leads 14 are coupled to IMD 10 via a connector block 11. Examples of cardiac stimulation or monitoring devices with which the present invention may be employed are generally disclosed in U.S. Pat. No. 5,545,186 (Olson et al.), U.S. Pat. No. 5,987,352 (Klein et al.), and U.S. Pat. No. 6,438,408 (Mulligan et al.), all of which patents are incorporated herein by reference in their entirety.

IMD 10 is in telemetric communication with EMD 22 to allow data stored or being acquired by IMD 10 to be retrieved by EMD 22 during an interrogation or monitoring session. EMD 22 can also be used to transfer code, operating parameters, or other instructions to IMD 10. Exemplary external devices that may be located in a patient's home having telemetric communication with an IMD are disclosed in U.S. Pat. No. 6,647,299 (Bourget), U.S. Pat. No. 6,564,104 (Nelson et al.), U.S. Pat. No. 6,561,975 (Pool et al.), U.S. Pat. No. 6,471,645 (Warkentin et al.) and U.S. Pat. No. 6,249,703 (Stanton et al.), all of which patents are incorporated herein by reference in their entirety.

Programming commands or data are transmitted between an IMD telemetry antenna 13 and an external telemetry antenna 15 coupled to the external device 22. The external telemetry antenna 15 may be contained in a programmer head so that it can be located close to the patient's skin overlying the IMD 10. Such programmer heads are well known in the art. See for example U.S. Pat. No. 4,550,370 (Baker), incorporated herein by reference in its entirety. The external device 22 may be designed to universally program IMDs that employ conventional ferrite core, wire coil, RF telemetry antennas known in the prior art and therefore also have a conventional programmer RF head and associated software for selective use with such IMDs.

Alternatively, the external telemetry antenna 15 can be located on the case of the external device 22, and the external device 22 can be located some distance away from the patient 12. For example, telemetry antenna 15 may be integrated with external device 22 and external device 22 may be located a few meters or so away from the patient 12 and utilize long-range telemetry systems. Such long-range telemetry systems may be preferable over systems requiring a programmer head such that passive telemetry transmission may occur between IMD 10 and external device 22 without patient interaction when IMD 10 is within a communication range of external device 22. Thus, patient 12 may be active, e.g., partaking in normal household activities or exercising during a telemetry transmission. Telemetry systems that do not require the use of a programmer head are generally disclosed in U.S. Pat. No. 6,240,317 (Villaseca et al.), U.S. Pat. No. 6,169,925 (Villaseca et al.), and U.S. Pat. No. 6,482,154 (Haubrich et al.), all of which patents are incorporated herein by reference in their entirety.

In an uplink telemetry transmission 17, the external RF telemetry antenna 15 operates as a telemetry receiver antenna, and the IMD RF telemetry antenna 13 operates as a telemetry transmitter antenna. Conversely, in a downlink telemetry transmission 19, the external RF telemetry antenna 15 operates as a telemetry transmitter antenna, and the IMD RF telemetry antenna 13 operates as a telemetry receiver antenna. Each RF telemetry antenna is coupled to a transceiver including a transmitter and a receiver. Any of a number of suitable programming and telemetry methodologies known in the art may be employed such as the RF encoded telemetry signal system generally disclosed in U.S. Pat. No. 5,312,453 (Wyborny et al.), incorporated herein by reference in its entirety. Other forms of wireless communication other than RF communication may be used in establishing uplink 17 and downlink 19 transmissions between IMD 10 and EMD 22.

External device 22 is shown in FIG. 1 to be embodied as a "programmer" or home monitor used in conjunction with IMD 10. Programmers are well known in the art and generally include a display 24, user interface 26, and a control system typically in the form of one or more microprocessors in addition to the telemetry circuitry described above. However, the present invention is not limited to being practiced with an IMD system wherein the external device functions as an associated programmer or home monitor. The present invention may alternatively be practiced with an external medical device system wherein a bedside or portable device performs physiological monitoring or therapy delivery functions. For example, EMD 22 may alternatively be embodied as a bedside monitoring console that may include ECG monitoring, blood pressure monitoring, oxygen saturation monitoring, carbon dioxide monitoring, or other physiological signal monitoring. Whether EMD 22 is associated with an internal or external medical device system, EMD 22 is provided with a communication link 28 that allows external device 22 to receive information from and transfer information to a centralized programmer 32.

Central programmer 32 may be implemented on a networked computer located at a clinical center or other patient management facility and can be part of an expert system used for remotely managing patients prescribed with medical monitoring or therapy delivery devices. Central programmer 32 may be implemented on an Internet-enabled computer system or a computer system on a local area network (LAN), wide area network (WAN), telecommunications network, or the like, which allows communication link 28 to be established between central programmer 32 and EMD 22 (or directly with IMD 10). Central programmer 32 includes a processor 34 that operates with an associated central database 36 used for storing patient data and for storing programs and algorithms used by the central programmer processor in performing patient management operations. As such, central database 36 may include electronic medical records in a relational database. Central database 36 further includes data files and code used for performing patient management operations and for controlling communication with the remote EMD 22 or IMD 10, which may include both programming and interrogation operations.

In other embodiments, central programmer 32 is implemented on a host server 30 accessible to a user via a web browser operating on a personal computer. Programs and algorithms for controlling patient management operations and communications with EMD 22 or IMD 10 may be stored in a database associated with host server 30. Host server 30 may store and execute algorithms used to set-up and control the application of customized workflow preferences in accordance with the present invention. In still other embodiments, remote patient management operations may be implemented in a distributed manner across a system including a host server 30 and a networked computer at a medical facility. For example, host server 30 may perform data conversion and processing and analysis of data received from the remote EMD 22 or IMD 10 and transfers the data to a networked computer at a medical facility where remote patient management operations are performed according to previously programmed customized workflow settings.

A user may program customized workflow preferences using an interface 38, typically a graphical user interface. In one embodiment, a user selects parameters relating to information contained in or relating to a remote medical device transmission which are used to select a set of workflow preferences. In another embodiment, the system "learns" customized workflow preferences as a set of "best practices" preferences by monitoring the type and frequency of requested patient management operations. In yet another embodiment, typically recommended patient management operations may be stored as default "best practices" workflow.

It is recognized that remote patient management operations performed according to customized workflow preferences as provided by the present invention may be embodied in a variety of medial device systems, which may include various implantable devices alone or in combination with other IMDs, various types of EMDs alone or in combination with IMD(s) and telemetry systems used for communicating with the IMD(s), and various embodiments of a central programmer 32 and communication link 28. Central programmer 32, for example, may be a dedicated instrument or may represent programming functionality implemented in software on an existing networked computer system or host server. Communication link 28 may be established via a hardwired modem connection or wireless communication technologies. Examples of remote monitoring/programming systems are generally disclosed in U.S. Pat. No. 6,599,250 issued to Webb et al., U.S. Pat. No. 6,442,433 issued to Linberg, and U.S. Pat. No. 6,574,511 issued to Lee, U.S. Pat. No. 6,480,745 issued to Nelson et al., U.S. Pat. No. 6,418,346 issued to Nelson et al., and U.S. Pat. No. 6,250,309 issued to Krichen et al., all of which patents are incorporated herein by reference in their entirety.

Figure 2:
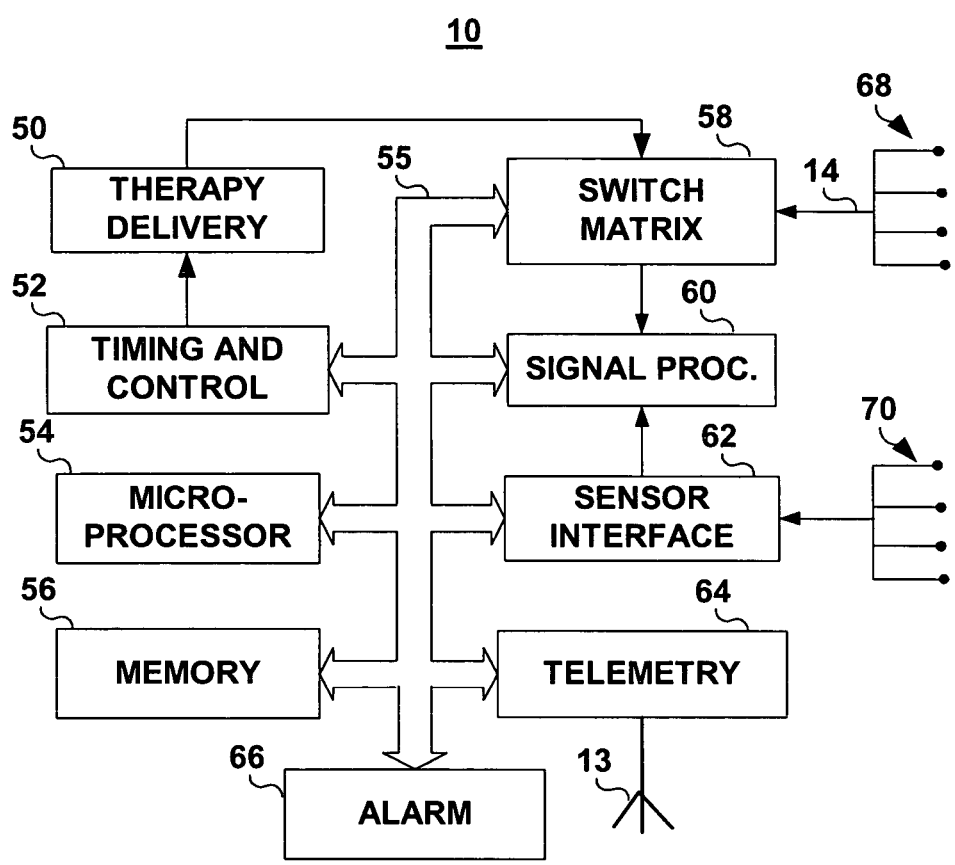
FIG. 2 is a block diagram of typical functional components of an IMD, such as the IMD shown in FIG. 1.

FIG. 2 is a block diagram of typical functional components of an IMD, such as IMD 10 shown in FIG. 1. IMD 10 generally includes timing and control circuitry 52 and an operating system that may employ microprocessor 54 or a digital state machine for timing sensing and therapy delivery functions in accordance with a programmed operating mode. Microprocessor 54 and associated memory 56 are coupled to the various components of IMD 10 via a data/address bus 55. IMD 10 may include therapy delivery unit 50 for delivering a therapy, such as an electrical stimulation or drug therapy, under the control of timing and control 52. In the case of electrical stimulation therapies, such as cardiac stimulation therapies, therapy delivery unit 50 is typically coupled to two or more electrodes 68 via a switch matrix 58. Switch matrix 58 is used for selecting which electrodes and corresponding polarities are used for delivering electrical stimulation pulses.

Electrodes 68 may also be used for sensing electrical signals within the body, such as cardiac signals, or for measuring impedance. In the case of cardiac stimulation devices, cardiac electrical signals are sensed for determining when an electrical stimulation therapy is needed and in controlling the timing of stimulation pulses. Electrodes used for sensing and electrodes used for stimulation may be selected via switch matrix 58. When used for sensing, electrodes 68 are coupled to signal processing circuitry 60 via switch matrix 58. Signal processor 60 includes sense amplifiers and may include other signal conditioning circuitry and an analog to digital converter. Electrical signals may then be used by microprocessor 54 for detecting physiological events, such as detecting and discriminating cardiac arrhythmias.

In other embodiments, electrodes 68 may be used for measuring impedance signals for monitoring edema, respiration or heart chamber volume. Any of these signals may be used to detect a change in a pathologic condition. Impedance signals can also be used for monitoring lead performance and detecting lead-related problems as is known in the art.

IMD 10 may additionally or alternatively be coupled to one or more physiological sensors 70. Such sensors may include pressure sensors, accelerometers or heart wall motion sensors, flow sensors, blood chemistry sensors, activity sensors or other physiological sensors known for use with IMDs. Sensors 70 are coupled to IMD 10 via a sensor interface 62 which provides sensor signals to signal processing circuitry 60. Sensor signals are used by microprocessor 54 for detecting physiological events or conditions. For example, IMD 10 may monitor heart wall motion, blood pressure, blood chemistry, respiration, or patient activity. Monitored signals may be used for sensing the need for delivering a therapy under control of the operating system. Physiological events or changes in monitored physiological conditions may serve as trigger events for causing storage of physiological data by IMD 10.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out upon receipt of a retrieval or interrogation instruction on a scheduled basis for remote patient monitoring. All of these functions and operations are known in the art, and many are generally employed to store operating commands and data for controlling device operation and for later retrieval to diagnose device function or patient condition.

IMD 10 further includes telemetry circuitry 64 and antenna 13. Programming commands or data are transmitted during uplink or downlink telemetry between IMD telemetry circuitry 64 and external telemetry circuitry included in a programmer or monitoring unit as described previously. Telemetry circuitry 64 and antenna 65 may correspond to telemetry systems known in the art. Microprocessor 54 controls telemetry operations for transmission of data from IMD 10 to central programmer 32 (shown in FIG. 1). Data transmissions may include and data acquired and stored by IMD 10 including device performance data and physiological data. Device performance data may relate to the history of monitoring and/or therapy delivery functions and data relating to automated device diagnostic functions. Physiological data may relate to any of the physiological signals or events monitored or detected by IMD 10.

In some embodiments, alert signals or messages may be generated in response to triggering events, which may be device-related or physiological events or conditions. Alert signal data may also be included in data transmissions to central programmer 32 (FIG. 1). IMD 10 may optionally be equipped with patient alarm circuitry 66 for generating audible tones, a perceptible vibration, muscle stimulation or other sensory stimulation for notifying the patient that a triggering alert condition has been detected by IMD 10.

Figure 3:
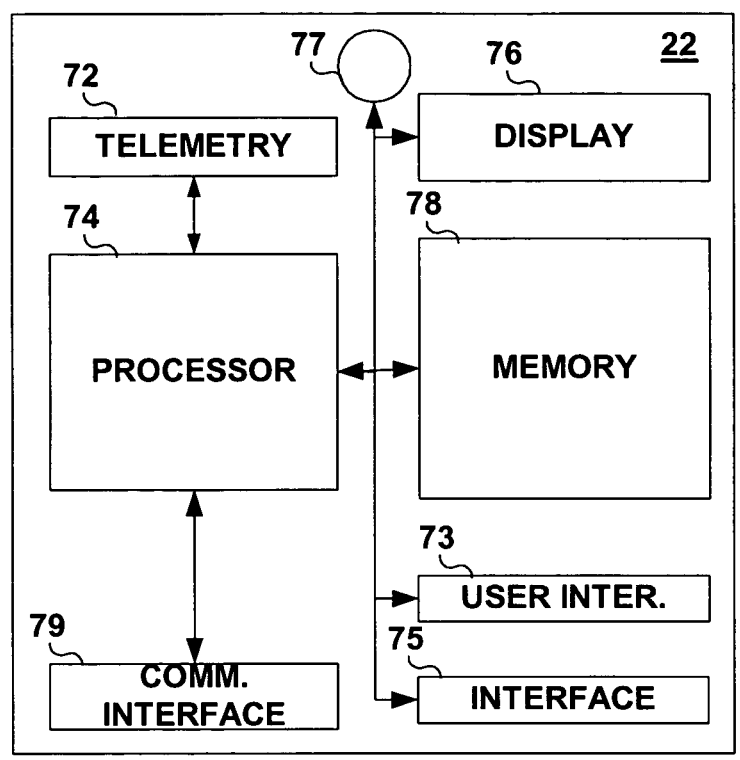
FIG. 3 is a functional block diagram of typical components included in an external medical device used for programming and retrieving data from an IMD, such as the external medical device shown in FIG. 1.

FIG. 3 is a functional block diagram of typical components included in an EMD used for programming and retrieving data from an IMD, such as EMD 22 shown in FIG. 1. EMD 22 is located at a remote location, such as a patient's home or in a clinic or other medical facility away from the centralized programmer. EMD 22 includes a communication network interface 79, such as a modem, used for communicating with central programmer 32 via a wireless or hardwired communication network. EMD 22 may act as communication conduit between the central programmer 32 (shown in FIG. 1) and IMD 10. EMD 22 transfers data retrieved from the IMD 10 to the central programmer 32 as described previously. EMD 22 may also transfer programming data received from the central programmer 32 to the IMD 10.

EMD 22 shown in FIG. 3 includes a telemetry circuit 72 for enabling bidirectional communication with IMD 10. EMD 22 includes a microprocessor 74 operating with associated memory 78 for controlling device functions, including telemetry and communication functions and any programming functions.

In order for a clinician, patient, or caregiver to interact with EMD 22, a keyboard, pointing device, or other user interface 73, coupled to microprocessor 74, is provided. Display 76, which may be embodied as a graphical user interface, and/or the user interface 73 allow a user to enter command signals to initiate transmissions of downlink or uplink telemetry and to initiate and control telemetry sessions once a telemetry link with an implanted device has been established. Other types of user interaction mechanisms and electronics may be implemented such as voice recognition/response systems. User interface 73 may also enable a patient or other caregiver to enter patient data such as patient weight, symptoms, location, or the like.

Display 76 may be included to display patient related data, menu choices and data entry fields used for entering data during a telemetry session. Display 76 can display a variety of screens of retrieved IMD data, previously stored or in real time and may display uplinked event signals as they are received and thereby serve as a means for enabling the user to review IMD operating history and status. Display 76 may be used for displaying messages to a user regarding communication and telemetry link status during the communication with a central programmer 32 and IMD 10. A speaker 77 may also be provided for broadcasting audible tones or messages used to alert the user to communication link, telemetry, programming, and/or interrogation status or conditions.

EMD 22 may further include an interface 75 for coupling peripheral devices which may include external monitoring equipment such as ECG leads, blood pressure monitor, etc. Data received by EMD 22 from IMD 10, from a user via user interface 73, or from another device via interface 75 may be included in transmissions sent to central programmer 32 for remote patient management purposes and used in selecting customized workflow preferences in accordance with the present invention.

Figure 4:
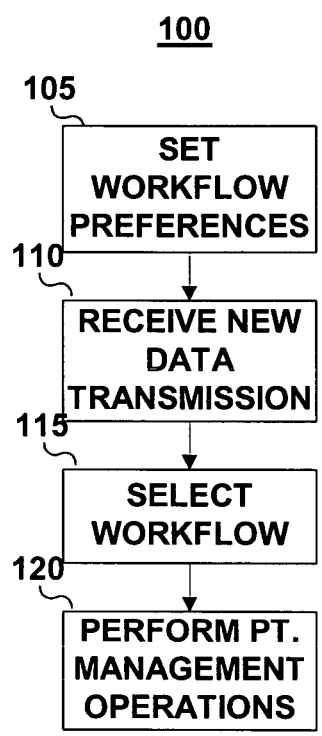
FIG. 4 is a flowchart summarizing steps included in a remote patient management method in accordance with the present invention.

FIG. 4 is a flowchart summarizing steps included in a remote patient management method in accordance with the present invention. At step 105, workflow preferences are set up by a user. The workflow preferences relate to the type and order of operations that will be performed by a central programmer upon receiving a data transmission from a remote medical device. The workflow preferences define which operations will be performed and what methods will be used to perform the operations. Workflow preferences may be defined based on information contained in the data transmission, such as the type and severity of physiological or device-related events. Workflow preferences may also be defined based on logistical conditions at the time of the transmission, such as the patient location relative to medical facilities or the clinical personnel available in a clinic or hospital or on call at the time of a transmission. Examples of transmission parameters that a user may select when programming customized workflow preferences at step 105 will be described in greater detail below.

Customized workflow preferences may be programmed by a user at step 105 as will be described below. According to an embodiment of the present invention, "best practice" workflow preferences may be stored by the central programmer. "Best practice" workflow preferences may be "learned" by the central programmer during a patient management session by tracking operations entered by a user. The user may request the central programmer to "learn" and store the workflow as the clinician steps through a series of operations as he/she reviews transmission data. Alternatively, "best practice" workflow preferences may be "learned" automatically over time by tracking the most frequently used operations in response to transmission data. Default "best practice" workflow preferences may be stored according to typically recommended operations performed for the type of device sending the transmission and the information contained in or relating to the transmission.

At step 110, a data transmission is received by the central programmer from a remote medical device. The central programmer selects the appropriate workflow at step 115 based on the information contained in the transmission or the time or related logistics at the time of the transmission. At step 120, the patient management operations are performed according to the selected workflow. If the operations are being performed according to a "best practices" workflow, the central programmer may prompt a user to accept or reject "best practices" operations that have been stored based on the history of frequently used operations.

Figure 5:
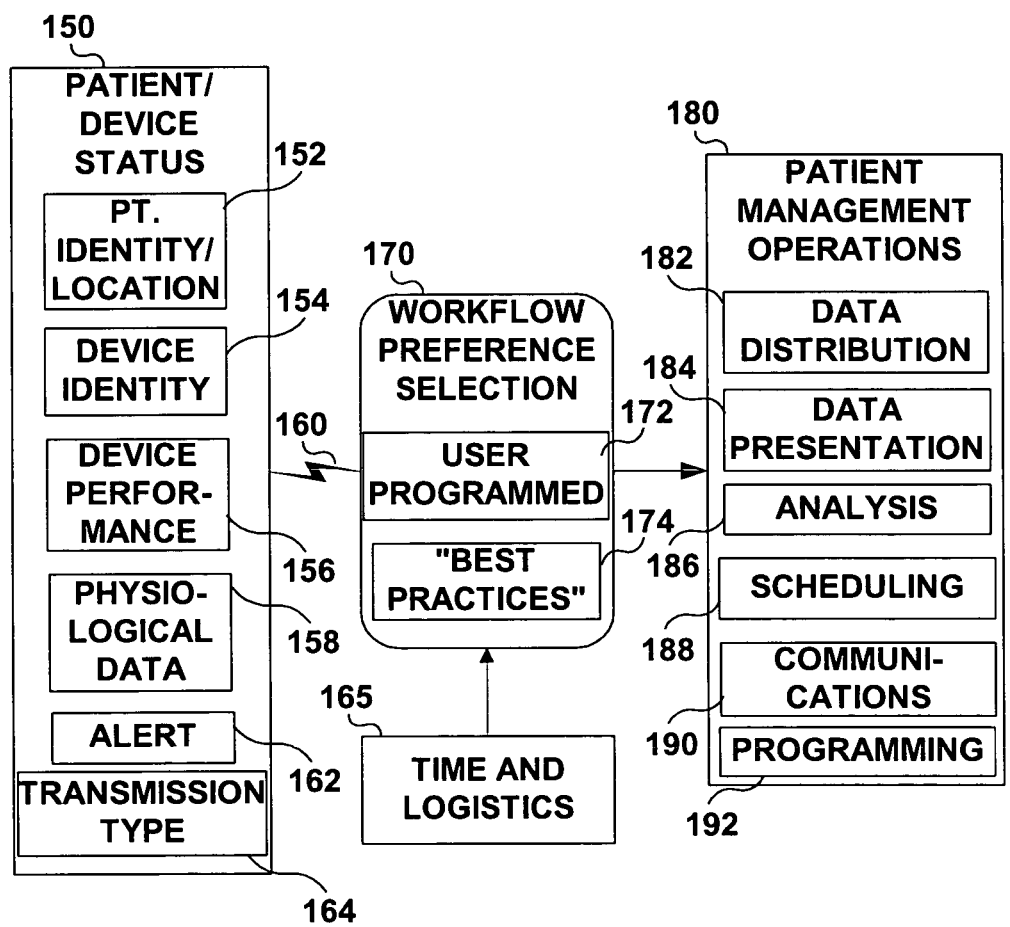
FIG. 5 is a functional block diagram illustrating the utilization of customized workflow methods in response to information contained in or relating to a data transmission received by a central programmer from a remote medical device.

FIG. 5 is a functional block diagram illustrating the utilization of customized workflow methods in response to information contained in or relating to a data transmission received by a central programmer from a remote medical device. In general, the device or patient status 150 corresponding to the transmission data causes workflow preference selection 170 according to user programmed 172 or "best practices" 174 customized workflow to be engaged by the central programmer for performing remote patient management operations 180.

The transmission receipt time and logistics 165 can also be used by the central programmer for selecting the workflow preferences 170. The time the transmission is received, the time since a previous transmission was received, and logistics relating to nearest medical centers and available personnel at the time the current transmission is received may be used for workflow preference selection 170. For example, if the transmission occurs on a weekend, a different workflow preference may be selected than during weekday office hours in order to notify or transfer transmission information to appropriate on-call medical personnel as necessary.

Furthermore, in some embodiments workflow preference may be selected at block 170 in response to the absence of an expected transmission. A maximum time elapsed since a previous transmission or a missed scheduled transmission may cause remote patient management operation to be performed according to selected workflow preferences. Such workflow may include sending communications to a patient or referring clinician to notify them that a transmission is overdue and automatically scheduling a transmission or an office visit.

The patient or device status 150 corresponding to the remote medical device transmission 160 may relate to the patient identity or geographical location 152, the medical device identity 154, device performance data 156, physiological data 158, alert signal data 162, and transmission type 164. Such data is included in the data transmission 160, and any parameter relating to such data may be previously programmed or learned as a parameter used for workflow preference selection 170.

The patient identity/location 152 may indicate or identify the patient according to primary and/or secondary diagnoses, known patient risk factors, patient medications, or other medical history. Such factors may be important in determining the prioritization, medical personnel involved, and other aspects of the remote patient management operations 180. As such, the patient identity may be a previously programmed or learned parameter used for workflow preference selection 170.

The patient identity/location 152 may alternatively or additionally identify or indicate the patient's geographical location. The patient could be traveling or otherwise away from home at the time of data transmission 160. Nearby medical centers and available medical personnel may be different than when the patient is at home. A change in the geographic location of the patient from his/her normal home location may therefore cause a change in the workflow preference selection 170. Patient location may be entered into an external medical device by the patient at the time of transmission or known by an IMD via GPS technology. Reference is made, for example, to U.S. Pat. No. 5,752,976, issued to Duffin et al., incorporated herein by reference in its entirety.

The device identity 154 can include the type of the remote medical device, the manufacturer and/or model of the device, a specific device serial number, and the presence of other co-existing medical devices, either implanted or external, associated with the patient. The type of device or specific serial number may indicate the type of data that will be available in a data transmission depending on device capabilities and individually programmed operating modes. As such, the workflow preference selection 170 may be based on device identity 154. For example, if the device is an ICD, arrhythmia episode and arrhythmia therapy data will be provided in a transmission. If the device is a multi-chamber pacemaker, the transmission may provide data relating to cardiac resynchronization therapies delivered and physiological data collected for heart failure monitoring. As such, the workflow may be customized for dealing appropriately with the various types of data available from a particular device.

Device performance data 156 includes any data stored and transmitted by the medical device relating to device diagnostic tests or records of delivered therapies or other device functions. Device performance data 156 may include, for example, an elective replacement indicator for an implantable device or other battery longevity indicator. In the case of cardiac stimulation devices, device performance data may include a history of delivered therapies such as the frequency of pacing, the number and type of arrhythmia therapies delivered, results from pacing threshold tests, and results from lead integrity tests. Drug delivery devices may store and transmit device performance data relating to the history of drug administration. A workflow preference selection 170 may be based on a change in or a particular level of a device performance parameter or a device alert signal relating to device status, such as an elective replacement indicator.

Physiological data 158 includes physiological data recordings or events detected and stored by the medical device included in transmission 160 to the central programmer. Physiological event data may also include data, for example patient weight or patient symptoms entered into the transmitting medical device by a patient or other caregiver or received from another medical device. A workflow preference selection 170 may be based on a change in a physiological condition or a physiological event detection. In the case of cardiac stimulation devices, a workflow preference selection may be made based on the detection of an arrhythmia or another detected change in the patient's heart rhythm. In cardiac monitoring devices, a workflow preference selection may be made based on a change in blood pressure, lung wetness, blood oxygen saturation, or other monitored parameter.

Some medical devices may be equipped with a patient alert module for notifying the patient or a clinician of a device-related or patient-related condition. Alert data 162 may be included in transmission 160 and used in selecting a workflow preference 170. In some embodiments, a patient alert signal may notify the patient that a data transmission is necessary. The device-related or physiological data causing the alert condition is transferred to the central programmer such that the appropriate workflow preference can be selected at block 170 and implemented by patient management operations 180 to cause a prompt medical response to the alert condition.

The transmission type 164 may influence workflow preference selection 170. For example, a different workflow may be selected depending on whether the transmission was a scheduled transmission or was initiated by the patient or a triggering event.

Various patient management operations 180 may be implemented or prioritized according to the workflow preference selection 170. Patient management operations 180 may include transmission data distribution 182, transmission data presentation 184, transmission data analysis 186, patient follow-up scheduling 188, communications 190, and remote medical device programming 192. Various data analysis operations 186 may be performed to evaluate patient condition based on physiological data received from the remote medical device or for evaluating device performance. Remote medical device programming operations 192 can include adjustment of operating parameters, altering programmed transmission schedules, or downloading software updates or new operating code to the remote device.

Figure 6:
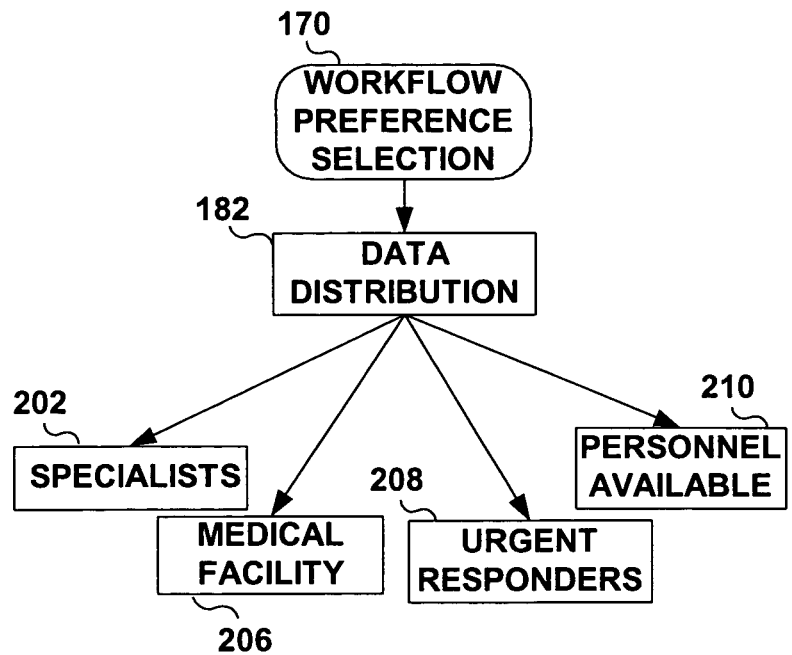
FIG. 6 is a schematic diagram summarizing data distribution operation that may be performed according a selected user-programmed or "best-practices" customized workflow.

FIG. 6 is a schematic diagram summarizing data distribution operation 182 that may be performed according a selected user-programmed 172 or "best-practices" 174 customized workflow. Transmission data received by a central programmer may be distributed to various clinicians and/or databases for review or storage. Workflow preference selection may define how transmission data is distributed based on patient/device status parameters 150 included in transmission 160 and/or transmission time and logistics 165 (as shown in FIG. 5). For example, data distribution operations 182 may be performed according to a workflow preferences selection 170 based on the type of transmission received (scheduled, alert-triggered, patient triggered, etc.), the type of information included in the transmission (device-related or physiological events), the time the transmission is received or the location of the patient at the time of the transmission and so on.

Transmission data may distributed to one or more selected clinical specialists 202 based on the type of information included in the transmission. In one embodiment, the remote patient management system may be used to monitor patients provided with an implantable cardioverter defibrillator (ICD) that includes some heart failure monitoring capabilities, such as blood pressure monitoring or lung wetness monitoring. If an arrhythmia event is included in a data transmission from the ICD to a central programmer, the data distribution list would include an electrophysiology cardiologist. If heart failure condition data is included in the data transmission from the ICD, such as an increase in lung wetness, a heart failure cardiologist may be included on a distribution list. In some cases, all transmission data may be distributed to one or more specialists. In other cases, a portion of the transmission data may be distributed to appropriate specialists.

Data distribution 182 may be performed according to workflow preferences selected based on patient location at the time of transmission. As such, transmission data may be distributed to one or more selected medical facilities 206. For example, the transmission data may be transferred to a clinician at a medical center located closest to the patient at the time of the transmission. In some cases, the data distribution operations 182 may be based on both the patient location and the transmission type or data included in the transmission. For example, a scheduled transmission that does not contain any device-related or physiological events that require medical attention may be distributed to the routine follow-up clinician and a database, regardless of patient location. An event- or patient-triggered transmission that contains event data that warrants urgent medical attention may be distributed to the routine follow-up clinician and to a clinician or emergency personnel at a medical center nearest the patient.

Data distribution operations 182 may be performed according to the urgency of the data included in the transmission. As such, data distribution may include urgent responder 208 or urgent care facility. Furthermore, distributed data determined to be urgent based on a device-related or physiological event or an alert condition may be labeled or marked as urgent or placed near the top of a list of data distributions for a clinician to review.

Data distribution 182 may be performed according to the time of the data transmission in order to provide the data to medical personnel available 210. As such, if a data transmission occurs after clinic hours or on a weekend, the data may be distributed to clinicians or medical personnel available according to an "on-call" or "after hours" schedule.

Figure 7:
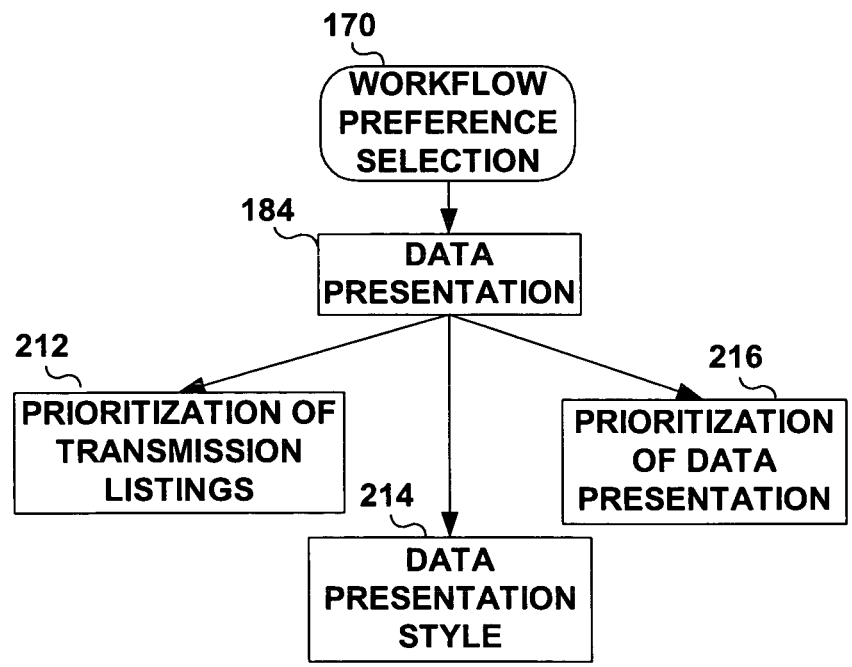
FIG. 7 is a schematic diagram of data presentation operations that may be performed according to a remote patient management workflow preference selection.

FIG. 7 is a schematic diagram of data presentation operations 184 that may be performed according to a remote patient management workflow preference selection 170. Data presentation operations 184 may include a prioritization of multiple transmission listings 212, selection of data presentation style 214, and a prioritization of transmission data presented 216.

A user-programmed or best practices workflow may define in what order data transmissions are listed for review. Numerous transmissions may occur between reviews by a clinician. Transmissions that may accumulate for review can include multiple transmissions from the same patient and transmissions from several different patients. As such, a user may select the order in which he/she prefers the transmissions to be listed for review. Transmissions that are triggered by an event detection, alert condition, or patient trigger may be listed with greater priority than regularly scheduled transmissions. In other workflow preferences, transmissions may be prioritized according to patient identity or device type such that transmission received from patient's having more serious or life-threatening conditions or other identified risks are listed with greater priority than other transmissions.

A clinician may have a preferred presentation style for enabling efficient review of the data. For example, some clinicians may prefer tabular presentations of data; others may prefer graphical presentations of data, and so on. As such, a user may select preferences for the data presentation style 214. Other formatting preferences may also be selected for use during data presentation operations such as text styles, colors, and the like.

After selecting a data transmission to be reviewed, the data included in the transmission is presented according to prioritization preferences 216 made according to user-programmed or a "best practices" selection. Prioritization of data presentation 216 allows a user to select customized views of transmission data in which selected data may be presented first or otherwise highlighted. For example, alert conditions, changes in a physiological condition, changes in a device-related condition, or other events may be formatted and presented in an order according to a user's preferences. Data may be presented in layered windows. For example, alert and other summary information may be presented in a primary window with supporting data presented in secondary windows. Supporting data may also be presented and formatted according to user preferences. In some embodiments, parameters that have changed since a previous transmission are highlighted or otherwise conspicuously formatted.

In some embodiments, data presentation prioritization 216 is selected in response to programmed "watch" events. A clinician may program one or more device-related or physiological events as triggers for prioritizing the transmission data for an individual patient or a population of patients. For example, if an arrhythmia therapy has been delivered, transmission data relating to arrhythmia episodes and other electrophysiological data may be presented first with other physiological data and device-related data presented secondarily. If a heart failure monitoring parameter has changed, such as a lung wetness parameter, blood pressure, heart rate variability or other heart failure monitoring data may be presented first with arrhythmia episode information and device-related data presented secondarily.

Figure 8:
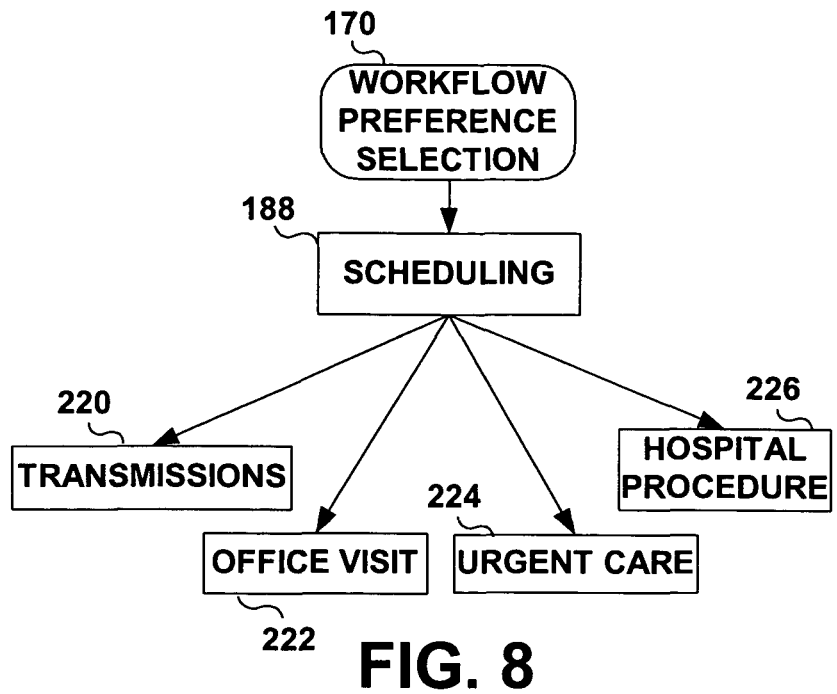
FIG. 8 is a schematic of scheduling operations that may be performed according to a remote patient management workflow preference selection.

FIG. 8 is a schematic of scheduling operations 188 that may be performed according to a remote patient management workflow preference selection 170. Scheduling operations 188 may include altering the schedule for receiving automatic data transmissions 220 from a remote device, scheduling an office visit 222, scheduling urgent care 224, and scheduling a hospitalization or procedure 226. Scheduling operations 188 are performed according to a workflow preference selection 170 made in response to information included in or relating to a received data transmission as previously programmed or "learned." For example, in response to a change in a device-related or physiological parameter, the frequency of medical device transmissions 220 may be increased or additional transmissions may be scheduled to allow closer patient monitoring.

A change in a device-related or physiological parameter may warrant an office visit. As such, office visit scheduling 222 may be performed automatically using electronic scheduling software. A change in a device-related or physiological parameter that reflects a serious condition for the patient may require urgent medical attention. Urgent care scheduling 224 may be performed automatically in response to a serious condition. Other conditions may require hospital procedure scheduling 226. For example, if an implantable device replacement indicator alert is received, a hospital procedure for replacing the implantable device can be scheduled.

Figure 9:
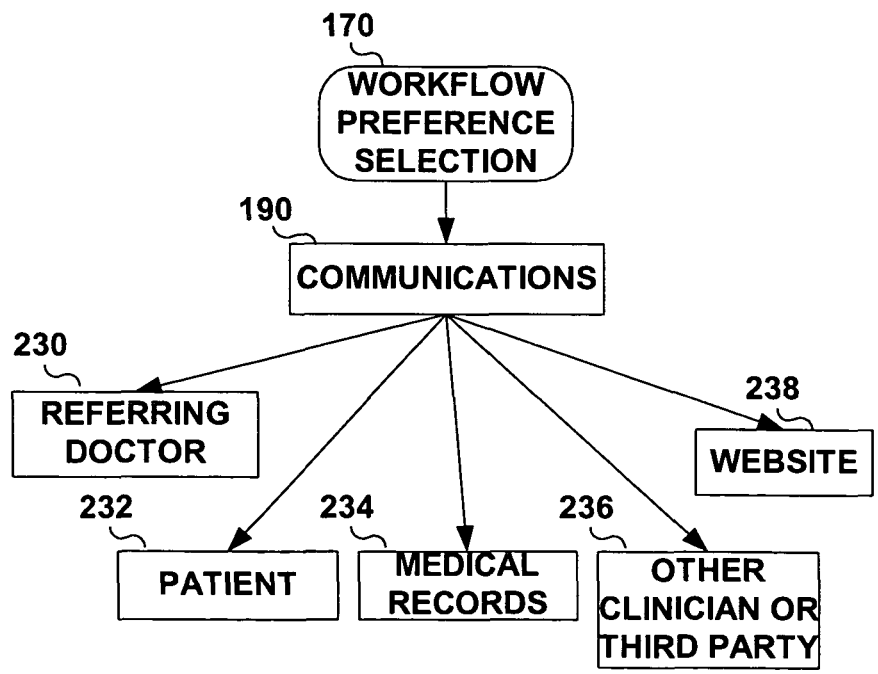
FIG. 9 is a schematic diagram of communications operations that may be performed according to a workflow preference selection.

FIG. 9 is a schematic diagram of communications operations 190 that may be performed according to a workflow preference selection 170. Communication operations 190 may include generation of letters, reports, billing, etc. that may be sent to a designated recipient electronically or printed for mailing. Communications operations 190 may involve sending a communication to the referring doctor 230, to the patient 232, to a medical records center 234 such as an electronic medical records database 234, to another clinician or third party 235, or to a website 238 for viewing by the patient or other authorized user. Communication operations 190 may be used to alert a clinician or the patient of a device-related or physiological event, an alert conditions, an automatically scheduled transmission, office visit or procedure. Communication operations 190 may also be used to perform automatic billing and medical records updates. The user-programmed or "best practices" workflow determines which communication operations are performed in response to a received transmission (or the lack of a received transmission) and in response to particular events or data included in a transmission.

Figure 10:
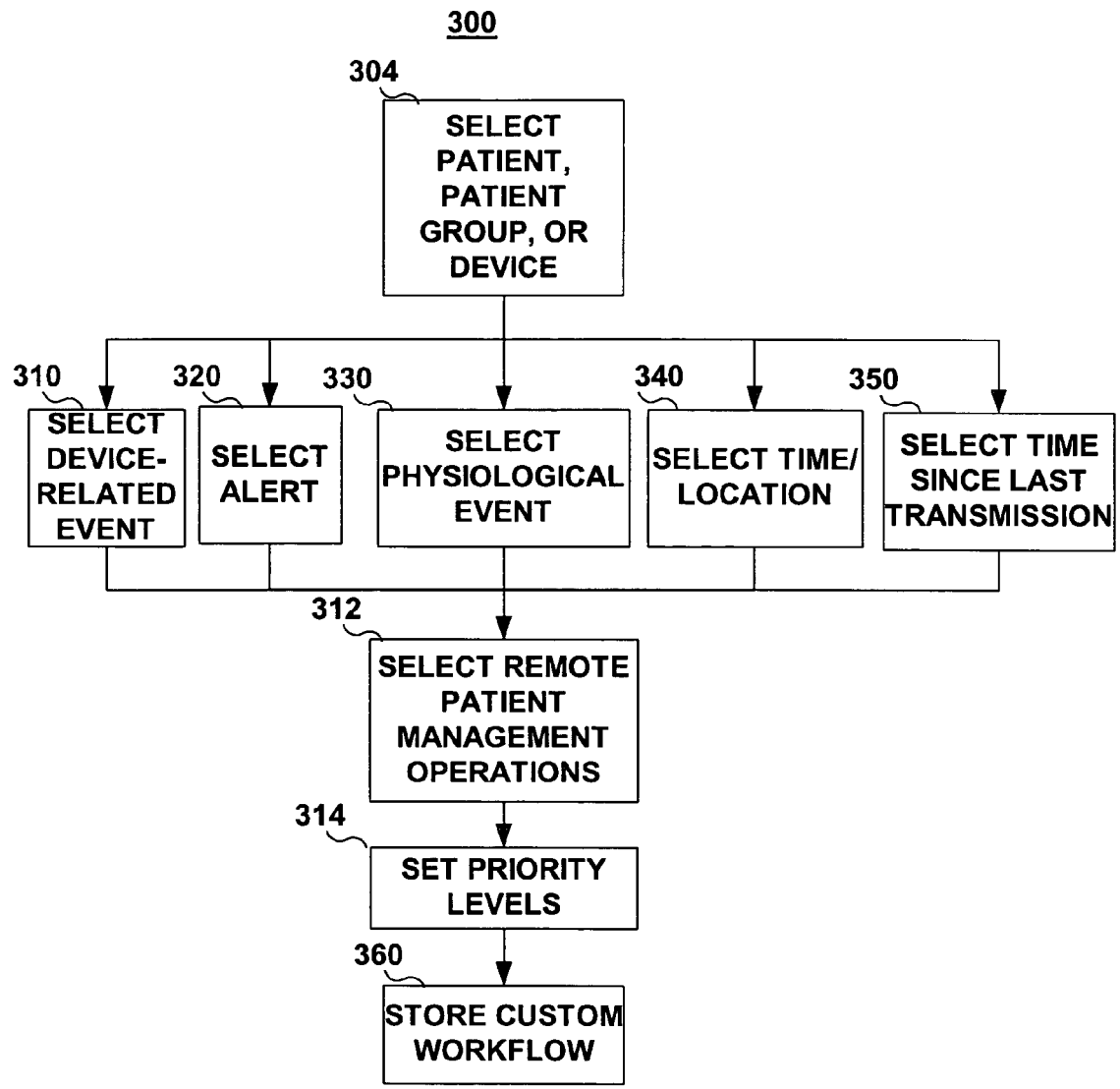
FIG. 10 is a flow chart summarizing a method for programming user customized workflow preferences.

FIG. 10 is a flow chart summarizing a method for programming user customized workflow preferences. Method 300 is performed by a user interacting with the central programmer. Software for performing user-programmed customized workflow set-up can be implemented on a networked computer or programmer or on a host server accessible by a web browser. In some embodiments, software for performing custom workflow set-up may be distributed across a remote patient monitoring system.

Generally, the user, interacting with the central programmer, typically with a graphical user interface (GUI), will step through a series of windows or screens that allow the user to select or enter various types of conditions or parameters relating to a remote medical device transmission for which a customized workflow is desired. The conditions that may be selected and the various choices for workflow operations will vary depending on the type of medical device, the medical condition being monitored or treated, and individual patient concerns. Therefore, method 300 in FIG. 10 is provided as a broad overview of an exemplary embodiment for setting up customized workflow preferences.

At step 304, a user selects the patient identity, the patient group, or the device identity or device models for which the custom workflow preferences are being set. Customized workflow preferences may be set up for individual patients as identified by a patient identity or device serial number. Customized workflow preferences may be set up for all patients having a particular device model. Customized workflow preferences may also be set up for a particular group of patients, for example, according to the referring clinician or primary diagnosis.

After selecting the patients or devices to which the customized workflow preferences will be applied, the user can select a number of transmission related parameters that will cause a customized workflow to be selected. In the example shown in FIG. 10, the user can select parameters relating to device-related events 310, alert signals, 320, physiological events 330, the time and location 340 of the patient at the time of the transmission or at the time of receipt by the central programmer, and time since last transmission 350.

At step 310, the user may select any of the available types of device-related events that may be reported in a data transmission from the remote device. Such events may include, for example, an elective replacement indicator, a lead-related event, a change in pacing threshold, and a history of delivered therapies. For each type of device-related event, the user may select, at step 312, the remote patient management operations to be performed in response to the selected device-related event. Remote patient management operations can include a customized distribution list, a scheduling operation, data analysis operations, data presentation preferences, a communication operation, and remote medical device programming as described previously.

At step 320, the user may select any of the alert signals that can be generated by the remote medical device. The user can select which workflow operations will be performed in response to a particular alert signal at step 312. At step 330, the user may select any physiological events that may be detected or stored by the remote medical device. Such events may relate to detected arrhythmia episodes, change in lung wetness, change in blood pressure, change in oxygen saturation, or any other physiological conditions which the medical device is capable of monitoring. At step 312, the user selects the operations to be performed in responding to the selected physiological event when it is included in a remote medical device transmission.

At step 340, the time and location of the patient at the time of the remote medical device transmission or receipt by the central programmer may be selected. The time may be identified according to office hours, after hours or weekends. The location may be identified as being home or away from home as indicated by the patient or according to GPS coordinates. Remote patient management operations are selected at step 312 to respond to the selected time or location parameter.

At step 350, the time since the last received transmission 350 may be selected and defined as a parameter used to select a workflow preference. If an expected transmission has not been received or if a maximum amount of time has elapsed, customized operations may be selected at step 312 to appropriately deal with the overdue transmission.

At step 314, the events or parameters for which customized operations have been defined may be assigned a priority level. The workflow preference selected in response to a remote medical device transmission may perform programmed operations according to the selections made for the highest priority event(s). Workflow operations may still be performed in response to lower priority events or transmission parameters if they do not conflict with high priority workflow operations.

The remote patient management system is enabled to perform checks such that redundancies in workflow operations are not performed in response to the same data transmission. For example, if an elective replacement indicator and a lead issue event are received in the same transmission and the workflow preference is set up to automatically schedule an office visit in response to both of these events, the system will schedule a single office visit with the appropriate clinician to address both events. However, if the workflow preferences are set up to automatically schedule an office visit in response to a heart failure related physiological event and a device-related event, the system may schedule separate office visits with different clinical specialists to appropriately address these separate events.

In another example, the same recipient may be included on distribution lists set up to respond to more than one event or transmission parameter. The system will verify that each recipient receives only one copy of the transmission distribution when more than one transmission parameter causes a distribution operation to be performed including one or more of the same recipients.

At step 360, the user can name and store a customized workflow. The customized workflow is implemented in response to a data transmission received from the patient, patient group, or device selected at step 304. Since multiple clinicians may use the remote patient management system, each clinician using the system is able to set-up, name and store his or her own customized workflow operations in accordance with personal practice preferences.

As described previously, customized workflow preferences may alternatively be "learned" over time or during a remote patient management session. When programming a set of customized workflow preferences, the user may have the option to select default or "best practice" workflow operations to be performed in response to any transmission parameters or events. The user may program customized workflow preferences for as few as one transmission event or parameter selection according to method 300 and rely on "learned" or default "best practice" workflow operations to control the response of the remote patient management system to all other transmissions. For example, the user may select a particular event, alarm or "watch" parameter for which a customized workflow is programmed. If the designated event, alarm or "watch" parameter is not included in a remote medical device transmission, the remote patient management system responds to the transmission according to the default or "best practices" workflow.

Thus, a remote patient management system and method for providing customized workflow operations according to clinician preferences has been described. It is recognized that one of skill in the art having the benefit of the teachings provided herein may conceive of variations to the embodiments described herein for providing customized remote patient management workflow. The detailed embodiments described herein, therefore, are intended to be exemplary and not limiting with regard to the following claims.

What is claimed is:

1. A method for remote patient management associated with a medical device, comprising:
   generating customized workflow instructions, including types and order of remote patient management operations in a central programmer;
   selecting a set of workflow instructions by the central programmer from the generated customized workflow instructions in response to data transmitted from a remote medical device to the central programmer;
   prioritizing the selected set of workflow instructions; and
   executing the selected set of workflow instructions by the central programmer in response to the prioritizing.

2. The method of claim 1, wherein the prioritizing is in response to one of device status, patient status, time of the data transmission, time since a previous data transmission, and source of the data transmission.

3. The method of claim 1, wherein the prioritizing is in response to one of patient identity, patient group and medical device identity.

4. The method of claim 1 wherein generating workflow instructions comprises automatically storing workflow instructions corresponding to frequently used workflow operations requested manually in response to transmitted remote medical device data.

5. The method of claim 1 wherein selecting the set of workflow instructions comprises selecting data distribution operations.

6. The method of claim 5, wherein selecting data distribution operations is based on a patient location and a transmission type or data included in a transmission.

7. The method of claim 1 wherein selecting the set of workflow instructions comprises selecting data presentation operations.

8. The method of claim 1 wherein selecting the set of workflow instructions comprises selecting automatic scheduling operations.

9. The method of claim 1 wherein selecting the set of workflow instructions comprises selecting data analysis operations.

10. The method of claim 1 wherein selecting the set of workflow instructions comprises selecting communication operations.

11. The method of claim 1 wherein selecting the set of workflow instructions comprises selecting remote medical device programming operations.

12. The method of claim 1, wherein the prioritizing is responsive to information included in the transmitted data.

13. The method of claim 1, wherein the central programmer receives data transmission from one of an implantable medical device or an external medical device.

14. A system for remote patient management, comprising:
   a remote medical device adapted to transmit data via a communication network;
   a central programmer coupled to the communication network for receiving data from the remote medical device, the central programmer comprising a processor for selecting workflow instructions associated with controlling remote patient management operations, wherein the workflow instructions are stored in a programmable memory according to a predetermined priority in response to receiving data from the remote medical device; and
   a user interface coupled to the central programmer to enable a user to generate the workflow instructions.

15. The system of claim 14, wherein the predetermined priority corresponds to one of device status, patient status, time of the data transmission, time since a previous data transmission, and source of the data transmission.

16. The system of claim 14, wherein the workflow instructions correspond to one of data distribution operations, data presentation operations, automatic scheduling operations, data analysis operations, communication operations, and remote medical device programming operations.

17. A method for remote patient management associated with a medical device, comprising:
   generating workflow instructions including remote medical device programming operations in a central programmer;
   selecting a set of remote medical device programming operations by the central programmer from the workflow instructions to send to a remote medical device, in response to data transmitted from the remote medical device to the central programmer;
   prioritizing the selected set of remote medical device programming operations according to workflow instructions; and
   executing the selected set of remote medical device programming operations in response to the prioritizing.

18. The method of claim 17, wherein the prioritizing is responsive to information included in the transmitted data.

19. The method of claim 17, wherein the prioritizing is in response to one of device status, patient status, time of the data transmission, time since a previous data transmission, and source of the data transmission.

20. The method of claim 17, wherein the prioritizing is in response to one of patient identity, patient group and medical device identity.

21. The method of claim 17, comprising:
   wherein executing the selected set of remote medical device programming operations includes sending the selected set of remote medical device programming operations to the remote medical device.

22. A system for remote patient management, comprising:
   a central programmer coupled to a communication network for receiving data from a remote medical device, the central programmer comprising a processor for selecting workflow instructions including remote medical device programming operations stored in a programmable memory according to a predetermined priority, in response to receiving data from the remote medical device; and
   wherein the central programmer is configured to send the selected workflow instructions to the remote medical device for execution.

23. The system of claim 22, further comprising the remote medical device, configured to transmit data via the communication network.

24. The system of claim 22, further comprising:
   a user interface coupled to the central programmer to enable a user to generate the workflow instructions.

* * * * *